United States Patent
Fox

Patent Number: 5,954,741
Date of Patent: *Sep. 21, 1999

[54] VENA-CAVA FILTER

[76] Inventor: Roger Harrington Fox, Aquarius, Ilsham, Marine Drive, Torquay, South Devon TQ1 2PN, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/750,905
[22] PCT Filed: Jun. 16, 1995
[86] PCT No.: PCT/GB95/01408
§ 371 Date: Dec. 13, 1996
§ 102(e) Date: Dec. 13, 1996
[87] PCT Pub. No.: WO95/34339
PCT Pub. Date: Dec. 21, 1995

[30] Foreign Application Priority Data

Jun. 16, 1994 [GB] United Kingdom .................. 9412092

[51] Int. Cl.[6] .................................................. A61M 29/00
[52] U.S. Cl. ................................ 606/198; 623/1; 623/12; 604/96; 606/200
[58] Field of Search ............................... 606/1, 108, 191, 606/194, 195, 198, 200; 604/96–100

[56] References Cited

U.S. PATENT DOCUMENTS

| | | | |
|---|---|---|---|
| 3,593,713 | 7/1971 | Bogoff et al. | 604/96 |
| 4,662,885 | 5/1987 | DiPisa, Jr. | |
| 4,723,549 | 2/1988 | Wholey et al. | |
| 5,501,667 | 3/1996 | Verduin, Jr. | 604/96 |
| 5,556,389 | 9/1996 | Liprie | 604/96 |

FOREIGN PATENT DOCUMENTS

| | | |
|---|---|---|
| 0377749 | 7/1990 | European Pat. Off. |
| 2580504 | 10/1986 | France |

*Primary Examiner*—Michael Buiz
*Assistant Examiner*—William Lewis
*Attorney, Agent, or Firm*—Hopgood, Calimafde, Kalil & Judlowe

[57] ABSTRACT

A vena-cava filter features an inflatable balloon at or near the distal end of an elongate flexible multiple-lumen core or stem. The balloon is suitably configured in a preferred construction at or near the distal end of an elongate flexible multiple-lumen core. The balloon is suitably configured in a preferred embodiment for femoral-vein insertional installation; and in another embodiment the balloon is suitably configured for jugular-vein insertional installation. In both embodiments, the balloon is deflated prior to insertion; it is inflated to become a filter when properly positioned in the vein, and finally it is deflated for removal purposes. Installation may proceed pursuant to guide-wire techniques commonly used for catheter installation. Each of the indicated two embodiments is described for the case of additionally providing for injection of a tracer or a thrombolytic agent at a location in the vein at proximal (i.e., upstream) offset from the region of filter action.

23 Claims, 4 Drawing Sheets

VENA-CAVA FILTER

FIELD OF THE INVENTION

The invention relates to a filter construction of the sort which is adapted for venous installation, generally for femoral-vein and/or for jugular-vein installation, for enhanced assurance that a blood clot of lethal size will not enter. the heart. More particularly, the invention relates to such a filter for installation in the inferior vena cava, sometimes known as a vena-cava filter, or merely as a caval filter.

BACKGROUND OF THE INVENTION

Vena-Cava filters have been known and their use has been reported for more than twenty years, and the Review Article of Becker, et al., entitled "Inferior Vena Cava Filters—Indications, Safety, Effectiveness", *Arch. Intern. Med.*—Vol. 152, October 1992, acknowledges the commercial existence of at least six competitive varieties and provides an extensive bibliography of relevant papers. It suffices to indicate that these prior and current filter structures rely on guide-wire piloting techniques of installation but must be removed within 48 hours if they are not to become so trapped by tissue growth within the vein as to become potentially destructive of vein tissue should they be later removed. As a consequence, on many occasions, such filters have often had to stay in place, as a permanent fixture within the patient.

An expandable filamentary-mesh filter, made by Angiocor s.a.r.l. of Lille, France is an attempt to avoid this problem of wall-tissue growth, using mechanically actuated expansion of multiple helices, wherein the helices are of plastic filamentary material.

Other prior art vascular filter devices are disclosed in FR-A-2580504 and U.S. Pat. No. 4,662,885. Reference may also be made to U.S. Pat. No. 4,723,549 and EP-A-0377749.

BRIEF STATEMENT OF THE INVENTION

It is an object of the invention to provide an improved filter structure of the character indicated.

Another object is to provide such a filter construction that will not promote vein-tissue growth therein and which therefore can be safely removed after it has served its purpose, even though the time of its installation has greatly exceeded the time within which other filters have had to be removed if tissue damage was to be avoided.

A specific object is to provide a filter construction for filtration of venous flow within a living body, wherein an inflatable balloon is adapted upon inflation to so partially occlude the inferior vena cava as to pass venous flow without clots of pulmonary-artery or heart-threatening magnitude.

It is also a specific object to provide a filter construction which involves no wire or other metal contact with vein tissues when installed in a femoral vein.

Another specific object is to provide an inflatable filter construction which is installed in deflated state and which relies on pressure-fluid inflation to establish vein-filtering action.

A further specific object is to provide, in conjunction with a vena-cava filter, an option to inject tracer or contrast fluid, or a thrombolytic agent, into the filter-protected vein at a location of proximal (i.e. upstream) offset from the filter; more specifically, it is an object to provide for such angular distribution of fluid injection as to establish circumferentially diffused introduction of thrombolytic agent which can directly act on any incipient thrombus accumulation at the filter, thereby clearing the filter of thrombi.

The invention achieves the foregoing objects and provides further advantageous features in an inflatable balloon construction at or near the distal end of an elongate flexible multiple-lumen core. The balloon is suitably configured in a preferred embodiment for femoral-vein insertional installation; and in another embodiment the balloon is suitably configured for jugular-vein insertional installation. In both embodiments, the balloon is deflated prior to insertion; it is configured so that when inflated it becomes a filter when properly positioned in the vein, and it may simply be deflated for removal purposes. Installation may proceed pursuant to guide-wire techniques commonly used for catheter installation. Each of the indicated two embodiments is described for the case of additionally providing for injection of a tracer or a thrombolytic agent at a location in the vein at proximal (i.e. upstream) offset from the region of filter action.

Exemplary embodiments of the invention will hereinafter be described in detail in conjunction with the accompanying drawings.

DETAILED DESCRIPTION

Figure 1:
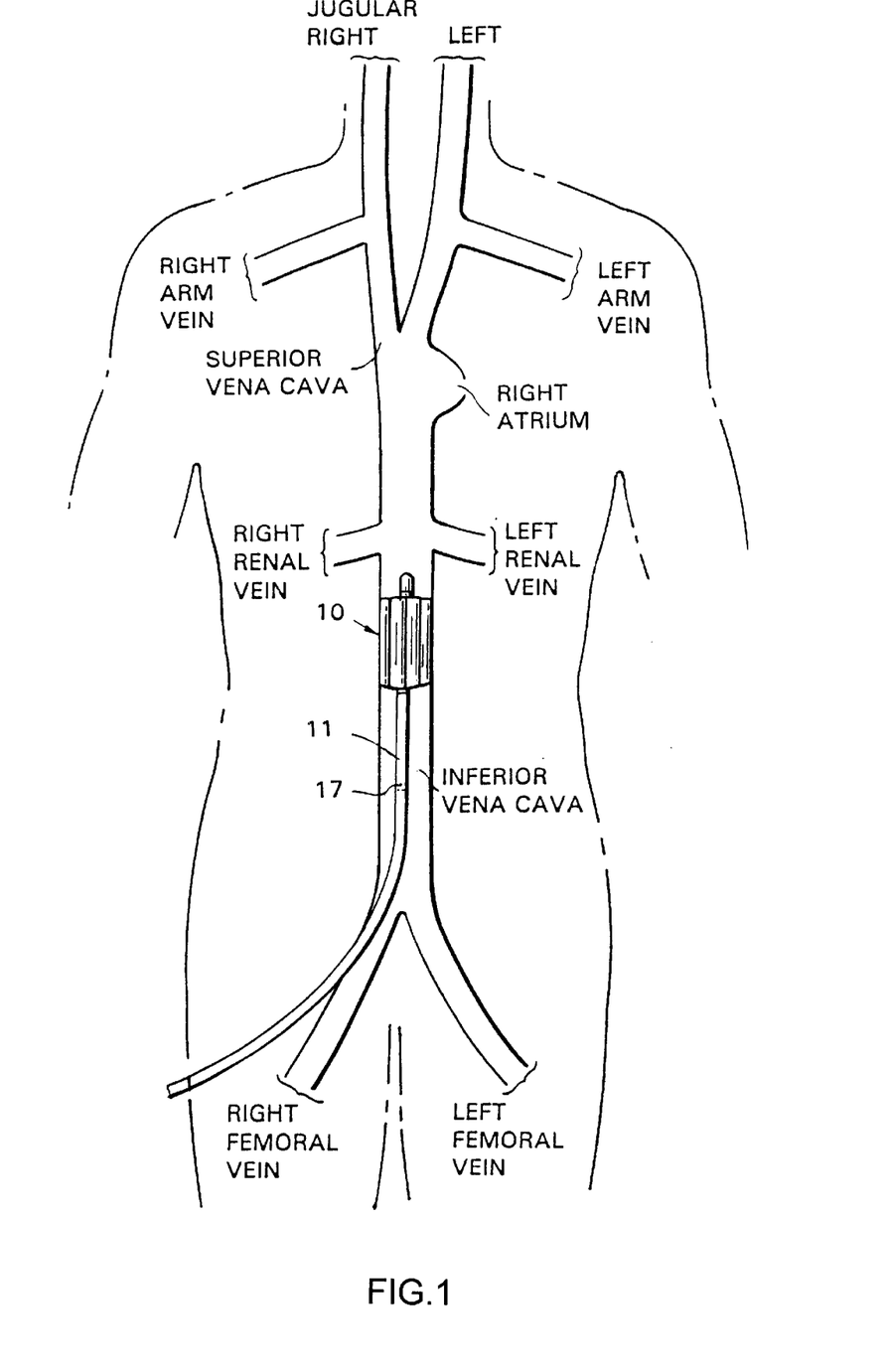
FIG. 1 is a simplified and somewhat schematic diagram to show the installed location of a first inflatable/deflatable embodiment of the invention.

The diagram of FIG. 1 provides body context for features of the principal veins to a patient's heart via the right atrium. An installed caval filter 10 of the invention is seen to comprise an inflated longitudinally fluted balloon at the distal end of an elongate multi-lumen stem 11. The filter will be understood to have been inserted, in deflated state, via one of the patient's femoral veins, here shown as the right femoral vein, and into the inferior vena cava at a region short of the renal veins and therefore proximal with respect to venous-return to the heart via the right atrium. The filter 10 is introduced into the body by way of conventional catheter-insertion procedures, which may rely upon an introducer and/or a guide wire. These procedures form no part of the invention and therefore need not be described, beyond noting that the stem 11 is flexible and has special provision for selective delivery of an inflating flow of pressure fluid to the balloon from an external source (not shown), or for extraction of pressure fluid from the balloon, in a deflation of the balloon, as in a procedure to remove the filter from the patient.

Figures 2, 3, 4:
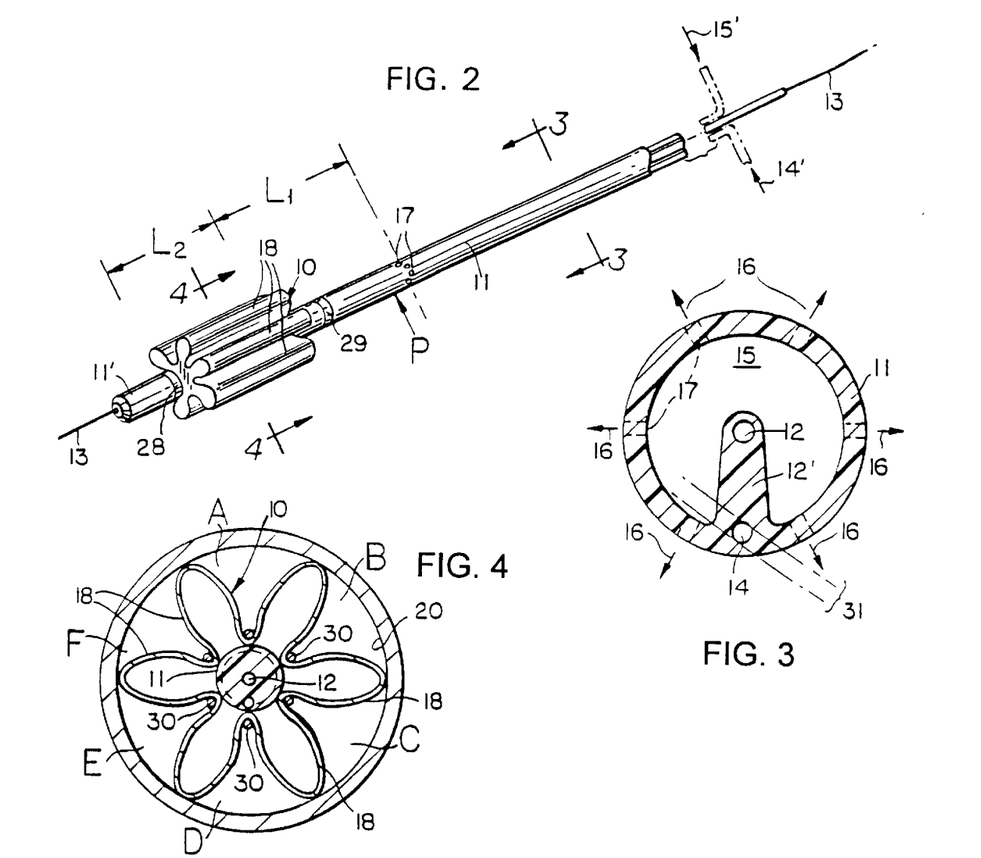
FIG. 2 is an enlarged view in perspective of the operative filtering distal end of the embodiment of FIG. 1 in inflated condition, the view being partly broken away to reveal internal features.
FIG. 3 is a greatly enlarged sectional view at 3—3 in FIG. 2.
FIG. 4 is a similar but less enlarged sectional view at 4—4 in FIG. 2.

In FIGS. 2 and 3, the filter 10 and its stem 11 are shown to have a central lumen or passage 12 at the inner end of a radial strut 12', for piloted guidance along a guide wire 13, and stem 11 has two further lumens, both of which are closed, at least at the distal end 11' of stem 11. One of these lumens provides a passage 14 for the pressure fluid to inflate or deflate the balloon, and the other lumen provides at 15 for flow of a medicating fluid, such as a contrast medium or a thrombolizing agent; external supply to these respective lumens is suggested at arrows 14', 15' in FIG. 2. In FIG. 3, plural further arrows 16 at equal angular spacing align with radial apertures 17 in the cylindrical wall of stem 11, providing uniformly distributed introduction of such fluid from lumen 15 and into the venous-return flow at a location of proximal offset $L_1$ from filter 10; the offset $L_1$ may be in the range of 3 to 10 centimeters, and preferably 5 to 7 centimeters. In FIG. 3 the apertures 17 are shown all at the same position longitudinally of the stem 11, but it will be appreciated that a spiral or other longitudinal spacing of the apertures 17 so as not to weaken unduly the stem wall is to be preferred, the apertures 17 preferably extending fully around the stem 11.

The balloon 10 intentionally partially occludes the local vena-cava section, by inflating to establish plural flutings or radial fins 18, shown in the drawings to be in a plurality of six, at equal angular spacing. These radial fins may be developed helically, for example with a steady angle of helical advance over the effective length $L_2$ of the balloon, in which case the passages 14 and 15 may likewise be of helically advancing nature with respect to the central passage 12 and the openings 17 may similarly follow a helical path. In the form shown the radial fins extend in planes parallel to and including the central axis of the filter, which in the wire-guided case shown is the axis of guide passage 12. In FIG. 4, the inner wall of the vena cava is seen at 20, and the stem or core 11 is stabilized by the inflated six contact alignments of fins 18, for substantially the full longitudinal extend $L_2$ of the filter.

Figure 6:
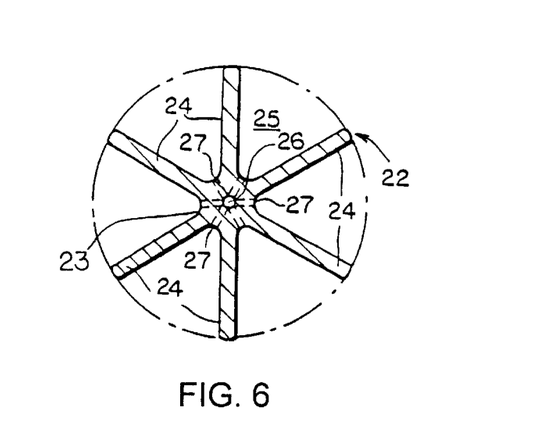
FIG. 6 is a right section of a moulding element for dip-moulding in manufacture of the inflatable element of FIG. 2.

More particularly, the plural fins 18 of balloon 10 are integral with each other, and the balloon itself may be manufactured from a moulding mandrel 22 having generally the cross-section shown in FIG. 6, namely, a central core 23 and plural radial fins 24. The core 23 will be understood to have cylindrical longitudinal ends which project beyond the distal and proximal ends of fins 24, these cylindrical ends are designed to develop a glove-like fit of the moulded balloon over and to the cylindrical outer surface of stem 11. The balloon 10 may be made by dipping the entire mandrel 22 in liquid elastomeric material such as latex and by allowing the same to cure, prior to extracting the moulded balloon from the mandrel, as by delivering a blast of pressurized air to the crotch 25 between each pair of adjacent fins 24; for this purpose, FIG. 6 shows a central longitudinal passage 26 and a separate radial alignment 27 for delivery of pressurized air into each crotch 25. With one end of passage 26 closed, and the other end supplied with compressed air, cured balloon material of fins 18 will strip from the mould fins 24 and will be stretched radially outward, enough to establish a clearance for removal from the mould. Having been cured prior to stripping, the moulded balloon can be readily returned to uninflated condition, and cut at its tubular ends, for assembly to the distal end of stem 11, the short distal ends of the balloon being circumferentially sealed and bonded to the cylindrical shape of the stem, as suggested at 28, 29 in FIG. 2.

The presently preferred construction of balloon 10 is completed by individual non-stretch reinforcing elements 30 (see FIG. 4), which may be filaments of wire or of suitable plastic material, taut in each crotch 25 and retained by longitudinally spaced bonds, such as those which at 28, 29 establish the sealed relation of balloon 10 to the stem 11. The elements 30 might alternatively be formed integrally with the balloon material, rather than as separate elements, and might for example be formed simply as a thickening of the balloon material at the appropriate locations, the balloon when inflated thus being intrinsically fluted without need for the element 30.

It will be understood that internal communication for passage of inflation/deflation fluid into and from balloon 10 may be via internal connection of passage 14 to each of the inflatable-fin structural features of the balloon. In the construction of the stem 11 in the region of prospective balloon-10 assembly thereto, the large lumen 15, for use in injection of a thrombolytic agent or other material, is closed by locally plugging the same at short distal offset from the plural apertures 17 (i.e., within the longitudinal space $L_1$), such plugged location being designated schematically at P in FIG. 2. That being the case, in the region distally beyond the plug at P and proximally of the distal end closure at 11', one or more axially spaced sets of radial apertures in the span $L_2$ of prospective balloon assembly to stem 11 may be provided in the stem wall at precisely the angular spacings shown in FIG. 3 for the radial apertures 17; and a skewed drill alignment, such as that suggested by phantom lines 31 in FIG. 3 (performed within the longitudinal region of the $L_2$ span of balloon assembly) may communicate inflation/deflation flows to and from the manifolding volume of lumen 15, within the span $L_2$. Once this drilled passage has been accomplished, a short plug of the outer open end of the drilled passage will close the same to external access, without interfering with passage 14 communication with lumen 15.

The balloon part of the filter assembly as thus described is shown in the drawings as having substantially squared proximal and distal ends. This, of course, need not be the case and it might be preferred for the ends of the balloon to taper or curve down to the stem 11.

In use, the filter assembly 10, 11 is installed via guide wire 13, with balloon 10 in fully deflated condition, wherein each of the radial fins 18 is fully collapsed and wrapped around stem 11. This wrapped condition is readily achieved by rotating the balloon and its fins in a single direction about the stem axis, while evacuating the balloon and progressively reducing its cylindrical circumference; the operation culminates in an umbrella-like wrap, depicted in FIG. 5. When sufficiently inserted to assume the desired position in the inferior vena cava, as shown in FIG. 1, inflation fluid, which may be a viscous liquid containing just enough of a contrast component for x-ray visibility, is injected at 14', causing fins 18 to inflate and assume their radially outward expansion into light equally spaced multiple self-stabilizing contacts with the inner surface of the vena-cava wall 20. Thus erected, balloon 10 occludes a significant fraction of the sectional area of the vena cava, and substitutes therefor a plurality of passages A, B, C, D, E, F of substantially triangular section for thereafter limiting passage of any blood clot to at least a small enough size as not to present a problem to the pulmonary artery or to the hear, i.e., to a size much reduced from a 7.5-mm clot size which otherwise might be lethal. Injection of a thrombolytic agent at 15' may commence at once for circumferentially diffused delivery to the situs of any thrombi trapped by one or more of the passages A to F, thus lysing such thrombi.

Figure 5:
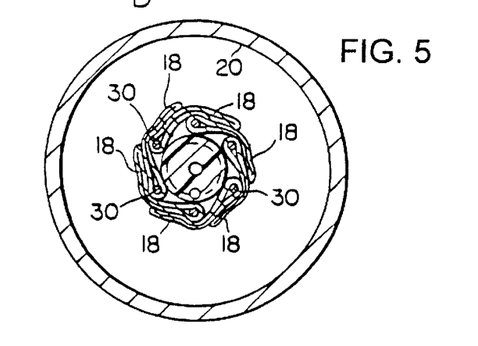
FIG. 5 is a view similar to FIG. 4, for the deflated condition.

Having used the described filter to the extend deemed necessary by the physician in charge, the described filter is removed by first deflating the same, preferably while rotating stem 11 to enable an umbrella-like wrap of deflated fins 18 to develop as seen in FIG. 5.

Figure 7:
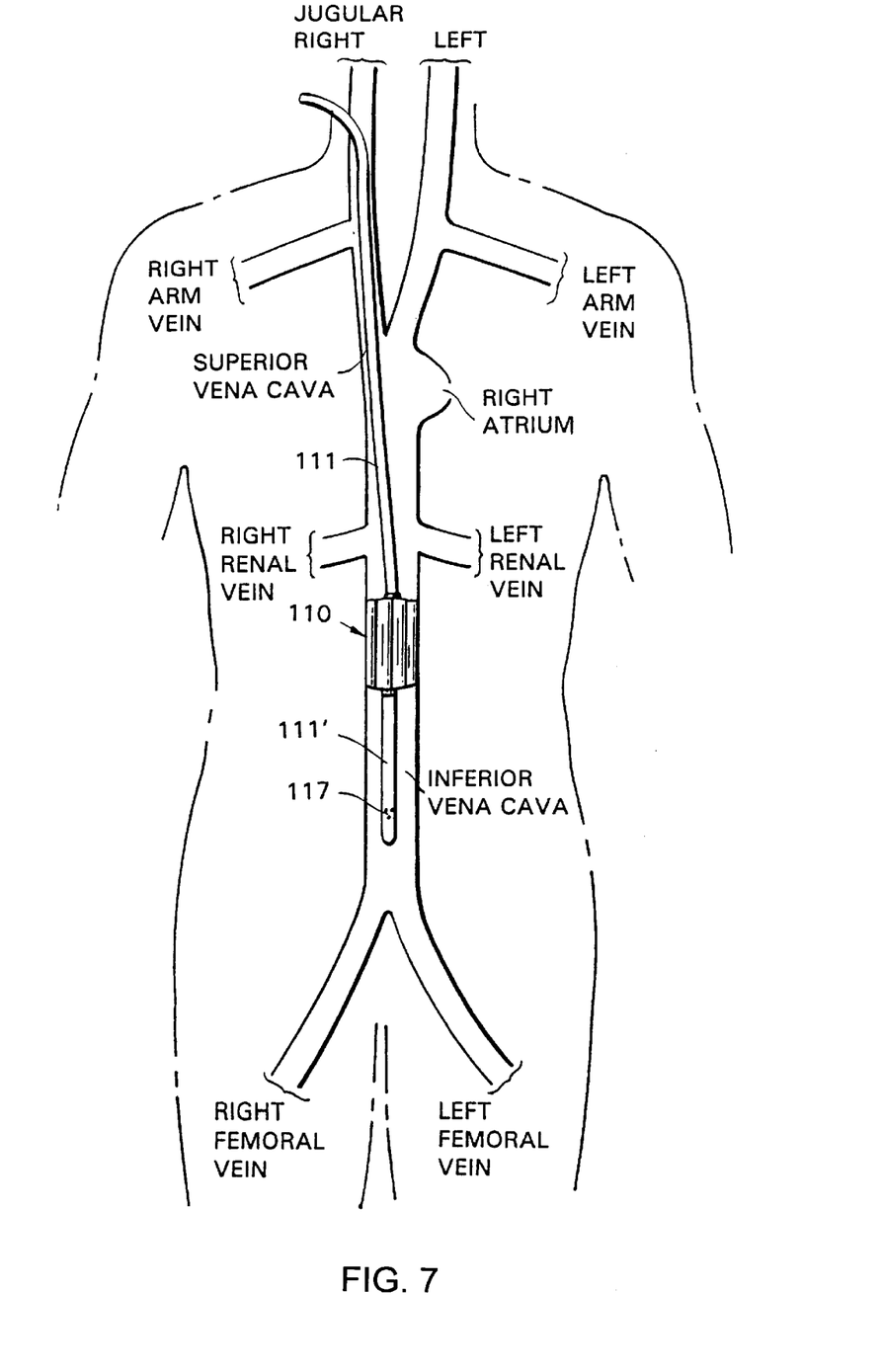
FIG. 7 is a view similar to FIG. 1 to show the installed location of a second inflatable/deflatable embodiment of the invention.
Figure 8:
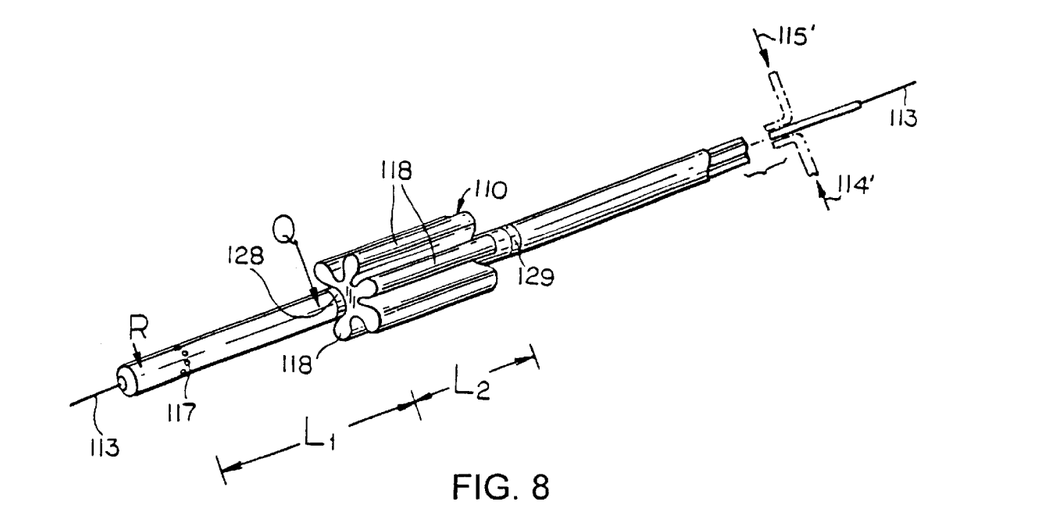
FIG. 8 is a view similar to FIG. 2, for the inflated condition of the second embodiment.

In FIGS. 7 and 8 parts that correspond to what has been described for FIGS. 1 to 6 are shown with the same numbers, but indexed in a 100-series. The embodiment of FIG. 7 is in virtually all its aspects the same as what has been described in connection with FIGS. 1 to 6, the differences being that in FIG. 7 (i) installation of the inflatable balloon 110 and its stem 111 is via the right jugular vein, through the superior vena cava, and past the right atrium and renal veins, for lodgement in the inferior vena cava as shown, and (ii) the distal end 111' of stem 111 projects distally beyond balloon 110, so that injection of a thrombolytic agent via apertures 117 may be sufficiently proximal with respect to venous flow to and through filter 110, and therefore proximal to any entrapped thrombi for ensuring optimal lysis of thrombus, to assure the previously described proximal offset $L_1$ from the filter.

More particularly, for the jugular-vein insertable device of FIGS. 7 and 8, the stem 111 section may be as described for stem 11 in connection with FIG. 3, but the use of this section is better dedicated to a reversal of functions for the externally served lumens 14, 15. Thus, for the case of FIGS. 7 and 8, it is preferred to utilize the large lumen 15 up to the location Q in FIG. 8, for inflation/deflation operation of balloon 110, lumen 15 being understood to have been locally blocked at Q, and of course both lumens 14, 15 being blocked at R, i.e., at the distal end of stem 111, i.e., distally of the location of the radial apertures 117. And in the region of stem 111 between locations Q and R, a skewed drilling as on the alignment 31 of FIG. 3 will establish exclusive communication between passage 14 and the relatively large volume of lumen 15; there being a small local external plug of the drilled alignment 31, for assurance of thrombolytic-agent delivery to lumen 15 and its circumferentially distributed apertures 117, at a vena-cava location that is at sufficiently proximal offset $L_1$ from the zone of inflated filter occlusion of the vena cava.

The invention will be seen to achieve all stated objects with relatively simple and easily operated structure which cannot become rooted in tissue growth within the vena cava. The structure may therefore remain within a patient for as long as his physician deems necessary, with facile, unharmful withdraw when desired, namely, long after the hitherto necessary time of 48 hours.

In the foregoing, there have been described inflatable/deflatable embodiments of the present invention wherein pressure fluid is delivered to a balloon for inflation of the device and is extracted therefrom for deflation. For the avoidance of doubt, it is to be understood that the pressure fluid could possibly be at atmospheric pressure, the balloon being formed with resilient structures such as will enable it to be deflated by suction and to be inflated by removal of the suction and exposure of the balloon interior to atmospheric pressure. By the same token, the inflation and deflation pressures could both be negative pressures relative to atmospheric pressure. Reference to inflation and deflation in the foregoing and in the appended claims should be construed accordingly.

Having thus described the invention by reference to exemplary embodiments it is to be well understood that modifications and variations are possible without departure from the spirit and scope of the invention as set forth in the appended claims. For example, the fluted balloon configuration of the described embodiments is not essential and any geometrical or other balloon shape which partly occludes the cross-sectional area of the vena cava could be utilized. In a simple form, the balloon could for example have a triangular, rectangular or other trapezoidal form.

I claim:

1. A vena-cava filter comprising an elongate flexible tubular core extending from a proximal end to a distal end, said core having at least one passage that is closed at the distal end, with at least one radially open side-port near the closed distal end, and an inflatable balloon carried by the distal end of the core with exclusive inflation/deflation access to said side-port, said balloon in inflated condition being adapted to engage angularly spaced locations of adjacent wall tissue of the inferior vena cava to the extent of only partially occluding the inferior vena cava and thus defining at least one longitudinal flow-channelling filter passage of reduced sectional area.

2. A vena-cava filter comprising an elongate flexible tubular core extending from a proximal end to a distal end, said core having at least two mutually independent passages that are closed at the distal end, at least one radially open first side-port connection to one of said passages near the distal end of said core and at least one radially open second side-port connection to the other of said passages near but proximally offset from said at least one first side-port connection, and an inflatable balloon carried near the distal end of said core with exclusive inflation/deflation access to one to the exclusion of the other of said first and second side-port connections, said balloon in inflated condition being adapted to engage angularly and symmetrically spaced locations of adjacent wall tissue of the inferior vena cava to the extent of only partially occluding the inferior vena cava and thus defining at least two longitudinal flow-channelling filter passages of reduced sectional area.

3. A vena-cava filter comprising an elongate flexible tubular core extending from a proximal end, to a distal end, said core having at least two mutually independent passages that are closed at the distal end, at least one radially open first side-port connection to one of said passages near the distal end of said core and at least one radially open second side-port connection to the other of said passages near but proximally offset from said at least one first side-port connection, and an inflatable balloon carried near the distal end of said core with exclusive inflation/deflation access to one to the exclusion of the other of said first and second side-port connections, said balloon in inflated condition being adapted to engage angularly and symmetrically spaced locations of adjacent wall tissue of the inferior vena cava to the extent of only partially occluding the inferior vena cava and thus defining at least two longitudinal flow-channelling filter passages of reduced sectional area, said balloon having exclusive inflation/deflation access to the more distally located one of said side-port connections whereby upon installation of the filter in the inferior vena cava via the femoral vein and upon inflation of said balloon to partially occlude the inferior vena cava, the more proximally located other side-port connections are adapted to provide access upstream of the partial occlusion for delivery of a thrombolizing or other agent into the partially occluded region of the inferior vena cava.

4. A vena-cava filter comprising an elongate flexible tubular core extending from a proximal end to a distal end, said core having at least two mutually independent passages that are closed at the distal end, at least one radially open first side-port connection to one of said passages near the distal end of said core and at least one radially open second side-port connection to the other of said passages near but proximally offset from said at least one first side-port connection, and an inflatable balloon carried near the distal end of said core with exclusive inflation/deflation access to one to the exclusion of the other of said first and second side-port connections, said balloon in inflated condition being adapted to engage angularly and symmetrically spaced locations of adjacent wall tissue of the inferior vena cava to the extent of only partially occluding the inferior vena cava and thus defining at least two longitudinal flow-channelling filter passages of reduced sectional area, said balloon having exclusive inflation/deflation access to the more proximally located one of said side-port connections, whereby upon installation of the filter into the inferior vena cava via the jugular vein and upon inflation of the said balloon to partially occlude the inferior vena cava, the more distally located other side-port connections are adapted to provide access upstream of the partial occlusion for delivery of a thrombolizing agent into the partially occluded region of the inferior vena cava.

5. A vena-cava filter comprising an elongate flexible tubular core extending from a proximal end to a distal end, said core having at least two mutually independent passages that are closed at the distal end, at least one radially open first side-port connection to one of said passages near the distal end of said core and at least one radially open second side-port connection to the other of said passages near but proximally offset from said at least one first side-port connection, and an inflatable balloon carried near the distal end of said core with exclusive inflation/deflation access to one to the exclusion of the other of said first and second sideport connections, said balloon in inflated condition being adapted to engage locally adjacent wall tissue of the inferior vena cava to the extent of only partially occluding the inferior vena cava, said balloon including means locally constraining said balloon against radial expansion at plural angularly spaced locations, whereby to develop the partial occlusion via plural angularly spaced passages of individual flow-channelling sectional area that is substantially reduced from the sectional area of the vena cava.

6. A filter, adapted for femoral-vein insertion into the inferior vena-cava of a living body, said filter comprising an elongate flexible tubular core extending from a proximal end to a distal end and having a generally cylindrical outer surface and a cross-section having a coaxially central continuous passage for insertional wire guidance, said central passage being one of three independent continuous passages wherein second and third passages are in angularly spaced relation in the body of the core and are radially interposed between the central passage and said outer surface; inflatable balloon material circumferentially bonded to said outer surface at two axially spaced locations near the distal end of said core, there being at least one side-port connection from said second passage and through said outer surface and at a location between said spaced axial locations for delivery of inflation fluid from said second passage to said balloon, there being at least one further side port communicating from said third passage and through said outer surface at an axial location near but proximally offset from said balloon material for delivery of a contrast agent or a thrombolizing agent via the third passage and at a location that is upstream of the filter when installed and balloon-inflated, and both said second and third passages being closed distally of their respective ports; and means associated with the balloon material for locally restraining radial expansion of the balloon at angularly spaced locations, said radial restraint being operative upon inflation to define a longitudinally fluted balloon development for angularly spaced stabilizing contact with the inner wall of the inferior vena cava thus leaving plural angularly spaced longitudinal filter passages of reduced sectional area between the inner wall of the vena cava and said angularly spaced balloon locations.

7. The filter of claim 6, in which said third-passage side port is one of a plurality of third-passage side ports.

8. The filter of claim 7, in which said second and third passages are of helically advancing nature about said central passage at least in the proximal region of said third-passage openings, said openings being arranged pursuant to the adjacent helical course of said third passage.

9. The filter of claim 8, in which the helical advance of said third passage is for a substantially full cycle of helical advance proximally with respect to said balloon material.

10. The filter of claim 6, in which the number of angularly spaced local restraints against expansion of balloon material is at least three, at equal angular spacing, whereby to establish stabilized central core positioning while also developing at least three equally angularly spaced filter passages.

11. A filter for jugular-vein insertion into the inferior vena-cava of a living body, said filter comprising an elongate flexible tubular core extending from a proximal end to a distal end and having a generally cylindrical outer surface and a cross-section having a coaxially central continuous passage for insertional guidance, said central passage being one of three independent continuous passages wherein second and third passages are in angularly spaced relation in the body of the core and are radially interposed between the central passage and said outer surface; inflatable balloon material circumferentially bonded to said outer surface at two axially spaced locations near the distal end of said core, there being at least one side-port connection from said second passage and through said outer surface and at a location between said spaced axial locations for delivery of inflation fluid from said second passage to said balloon, said second passage being closed distally of its side-port connection, and said third passage being distally open for delivery of a contrast agent or a thrombolizing agent via the distally open end of the third passage and at a location that is upstream of the filter when installed and balloon-inflated; and means associated with the balloon material for locally restraining radial expansion of the balloon at angularly spaced locations, said radial restraint being operative upon inflation to define a longitudinally fluted balloon development for angularly spaced stabilizing contact with the inner wall of the inferior vena cava, thus leaving plural angularly spaced longitudinal filter passages of reduced sectional area between the inner wall of the vena cava and said angularly spaced balloon locations.

12. The filter of claim 11, in which the distally open end of said third passage comprises a plurality of spaced radially outward openings in proximal adjacency to an otherwise closed distal end of said third passage.

13. The filter of claim 11, in which said second and third passages are of helically advancing nature about said central passage at least in the distal region of said radial outward openings, and said radially outward openings being arranged pursuant to the adjacent helical course of said third passage.

14. The filter of claim 13, in which the helical advance of said third passage is for a full cycle of helical advance distally beyond said balloon material.

15. The filter of claim 11, in which the number of angularly spaced local restraints against expansion of balloon material is at least three, at equal angular spacing, whereby to establish stabilized central core positioning while also developing at least three equally angularly spaced filter passages.

16. A filter, for intravenous insertion in the direction of return blood flow in a vein of a living body, said filter comprising an elongate flexible tubular core extending from a proximal end to a distal end and having a generally cylindrical outer surface and a cross-section having first and second independent continuous passages in spaced relation within said outer surface; inflatable balloon material circumferentially bonded to said outer surface at two axially spaced locations near the distal end of said core, there being at least one side-port connection from said first passage and through said outer surface and at a location between said spaced axial locations for delivery of inflation fluid from said first passage to said balloon, there being at least one further side port communicating from said second passage and through said outer surface at an axial location near but proximally offset from said balloon material for delivery of a contrast agent or a thrombolizing agent via the second passage and at a location that is upstream of the filter when installed and balloon-inflated, and both said first and second passages being closed distally of their respective ports; and means associated with the balloon material for locally restraining radial expansion of the balloon at angularly spaced longitudinally extending locations, said radial restraint being operative upon inflation to define a longitudinally fluted balloon development for angularly spaced stabilizing contact with the inner wall of the vein thus leaving plural angularly spaced longitudinal filter passages of reduced sectional area between the inner wall of the vein and said angularly spaced balloon locations.

17. A filter, for intravenous insertion in the direction opposite the direction of return blood flow in a vein of a living body, said filter comprising an elongate flexible tubular core extending from a proximal end to a distal end and having a generally cylindrical outer surface and a cross-section having first and second independent continuous passages in spaced relation within said outer surface; inflatable balloon material circumferentially bonded to said outer surface at two axially spaced locations near the distal end of said core, there being at least one side-port connection from said first passage and through said outer surface and at a location between said space axial locations for delivery of inflation fluid from said second passage to said balloon, said first passage being closed distally of its side-port connection and said second passage being distally open for delivery of a contrast or a thrombolizing agent via the second passage and at a location that is upstream of the filter when installed and balloon-inflated; and means associated with the balloon at angularly spaced longitudinally extending locations, said radial restraint being operative upon inflation to define a longitudinally fluted balloon development with angularly spaced stabilizing contact with the inner wall of the vein, thus leaving plural angularly spaced longitudinal filter passages of reduced sectional area between the inner wall of the vein and said angularly spaced balloon locations.

18. A method of installing a vena-cava filter in an inferior vena-cava, the filter comprising an elongate flexible tubular core extending from a proximal end to a distal end, with at least one radially open side-port near the closed distal end, and an inflatable balloon carried by the distal end of the core with exclusive inflation/deflation access to the side-port, the method comprising the steps of:
deflating the balloon;
circumferentially wrapping the balloon around the core;
opening an incision in a vein remote from and communicating with the inferior vena-cava;
inserting the distal end of the core, with the deflated circumferentially wrapped balloon, through the incision and remote vein into the inferior vena-cava to a desired longitudinal position along the length of the inferior vena-cava; and
inflating the balloon by increasing the fluid pressure in the tubular core such that outer axial sections of the balloon engage angularly spaced locations of adjacent wall tissue of the inferior vena-cava to the extent of only partially occluding the inferior vena-cava and thus defining at least one longitudinal flow-channelling filter passage of reduced sectional area.

19. The method of claim 18, in which the balloon is circumferentially bonded to two axially spaced locations of the outer surface of the tubular core, the two axially spaced locations being located in opposite axial directions relative to the side-port enabling delivery of inflation fluid from the interior of the core to the balloon, the filter having means associated with the balloon for locally restraining radial expansion of axial portions of the balloon at angularly spaced locations upon inflation of the balloon such that the balloon is fluted with plural radial fins, said step of circumferentially wrapping the deflated balloon around the core comprising rotating the core in a single direction about its longitudinal central axis producing concomitant rotation of the radial fins of the balloon contemporaneous with said step of deflating the balloon to progressively reduce the outer circumference of the balloon.

20. The method of claim 18, in which the balloon is circumferentially bonded to two axially spaced locations of the outer surface of the tubular core, the two axially spaced locations being located in opposite axial directions relative to the side-port enabling delivery of inflation fluid from the interior of the core to the balloon, the filter having means associated with the balloon for locally restraining radial expansion of axial portions of the balloon at angularly spaced locations upon inflation of the balloon such that the balloon is fluted with plural radial fins, the method further comprising the steps, after inserting the balloon into the inferior vena-cava and inflating the balloon, of:
rotating the core in a single direction about its longitudinal central axis producing concomitant rotation of the radial fins of the balloon contemporaneous with said step of deflating the balloon to circumferentially wrap the deflated balloon around the core thereby progressively reducing the outer circumference of the balloon; and
retracting the core from the incision sufficiently to withdraw the distal end of the core with the deflated circumferentially wrapped balloon from the inferior vena-cava and remote vein through the incision.

21. The method of claim 18, in which said step of inflating the balloon by increasing the fluid pressure in the tubular core comprises delivering a fluid having a contrast component for x-ray visibility.

22. The method of claim 18, in which the tubular core has at least two mutually independent passages that are closed at the distal end, one of the passages being connected to the side-port constituting a first side-port, the core having a second side-port located proximally relative to the first side-port, the second side-port being connected to the other passage,     said step of opening an incision in the remote vein comprising opening the incision in a femoral vein,     said step of inflating the balloon comprising increasing the fluid pressure in the one passage,     after said step of inflating the balloon, delivering a fluid having a thrombolizing agent to the other passage at a sufficient pressure such that the fluid exits the second side-port upstream of the partial occlusion for delivery of the thrombolizing agent into the partially occluded region of the inferior vena-cava for lysing a thrombus lodged against the balloon.

23. The method of claim 18, in which the tubular core has at least two mutually independent passages that are closed at the distal end, one of the passages being connected to the side-port constituting a first side-port, the core having a second side-port located distally relative to the first side-port, the second side-port being connected to the other passage,     said step of opening an incision in the remote vein comprising opening the incision in a jugular vein,     said step of inflating the balloon comprising increasing the fluid pressure in the one passage,     after said step of inflating the balloon, delivering a fluid having a thrombolizing agent to the other passage at a sufficient pressure such that the fluid exits the second side-port upstream of the partial occlusion for delivery of the thrombolizing agent into the partially occluded region of the inferior vena-cava for lysing a thrombus lodged against the balloon.

\* \* \* \* \*